United States Patent [19]

Kuhn et al.

[11] Patent Number: 5,044,210
[45] Date of Patent: Sep. 3, 1991

[54] METHOD AND MEANS FOR TESTING THE STRENGTH OF PLANT STALKS

[75] Inventors: Kevin W. Kuhn, Tipton; Stephen L. Letsinger, Kempton; Joseph W. Keaschall, Sharpsville; Charles T. Cunnyngham, Tipton; Alan P. Floyd, Elwood; Keith G. Freeman, Kirklin; James B. Ray, Tipton, all of Ind.

[73] Assignee: Pioneer Hi-Bred International, Inc., Des Moines, Iowa

[21] Appl. No.: 609,164

[22] Filed: Nov. 1, 1990

[51] Int. Cl.5 ............................................. G01N 3/20
[52] U.S. Cl. .................................................. 73/865.3
[58] Field of Search ........................ 73/865.3, 851, 849

[56] References Cited

U.S. PATENT DOCUMENTS 4,982,609 1/1991 Talley III. .............................. 73/849

Primary Examiner—Robert Raevis
Attorney, Agent, or Firm—Zarley, McKee, Thomte, Voorhees & Sease

[57] ABSTRACT

A device is provided for testing the strength of plant stalks. The device includes a frame adapted to be secured to a tractor or combine. An upright member is pivotally attached to the frame and has an arm extending substantially horizontally therefrom. A spring is connected between the upright member and the frame so as to provide biasing against the pivotal movement of the upright member and attached arm. In operation, as the tractor or combine moves along a row of plants, the arm engages each plant which bends over and breaks if the stalk is not sufficiently strong to resist the force of the forwardly moving arm. If the stalk is sufficiently strong, the stalk will bend but not break or the arm will pivot rearwardly until it passes by the stalk and then is automatically returned to its initial position.

3 Claims, 2 Drawing Sheets

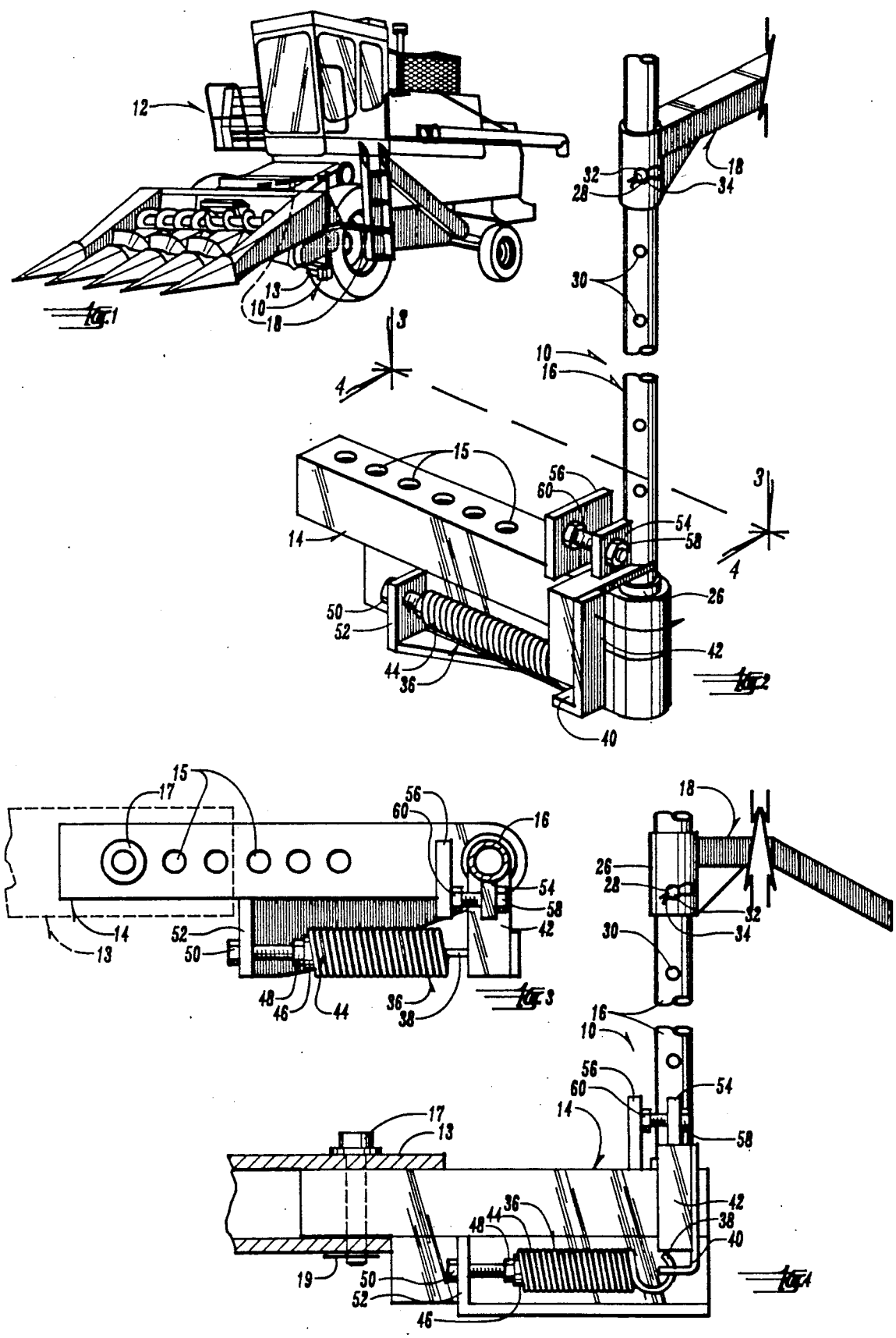

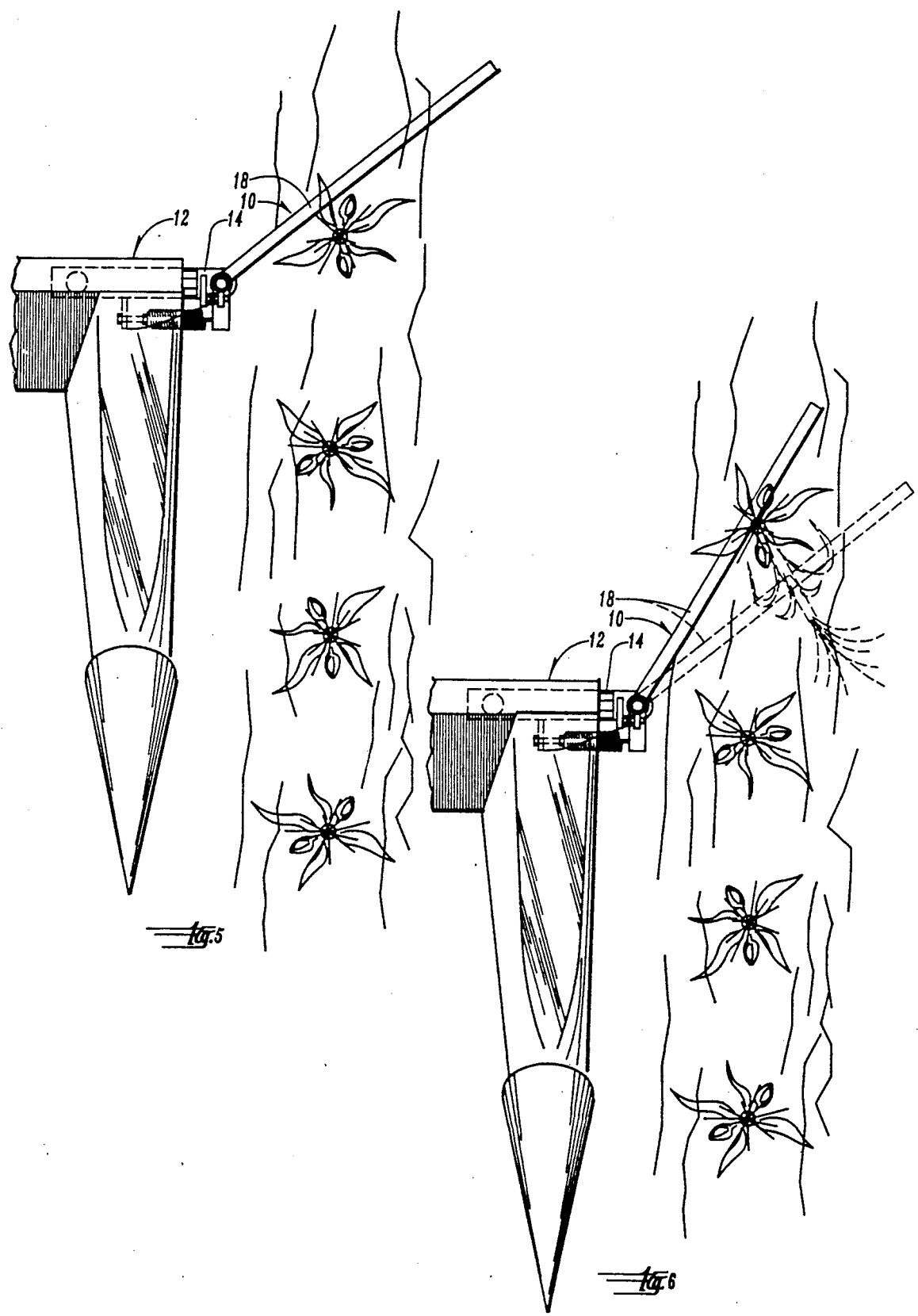

METHOD AND MEANS FOR TESTING THE STRENGTH OF PLANT STALKS

BACKGROUND OF THE INVENTION

In developing hybrid agricultural plants, such as corn, it is desirable to have plants with strong stalks so as to withstand adverse weather conditions. In the past, the research and development of hybrid plants has included a stalk strength test wherein the stalks were manually pushed with a person's hand or forearm as the person walked past the plants. This method of testing requires a separate crew to push the stalks prior to harvesting. Such hand pushing is strenuous, time consuming and costly.

Therefore, a primary objective of the present invention is the provision of an improved method and means for testing stalk strength.

Another objective of the present invention is the provision of a method and means of testing stalk strength which can be done simultaneously with the harvesting of the crop.

Still another objective of the present invention is the provision of a method and means for testing stalk strength which is simple and economical.

These and other objectives will become apparent from the following description of the invention.

SUMMARY OF THE INVENTION

A device is provided for testing the strength of plant stalks, such as corn, planted in a field. The device includes a frame which is mounted to a combine or tractor. An upright pipe is pivotally mounted to the frame and supports an elongated arm extending substantially horizontally from the pipe. A spring is provided on the frame and is operatively connected to the pipe so as to bias the pipe and attached arm against pivotal movement.

As the combine or tractor moves through the field, the outwardly extending arm engages each stalk. Stalks having sufficient strength to resist the force of the forwardly moving arm cause the arm to pivot rearwardly so as to slide by the stalk. On the other hand, weak stalks which are not sufficiently strong to resist the force of the forwardly moving arm are pushed over or broken by the arm. The general stalk strength of the test plot is judged by the percentage of stalks broken. This information can then be utilized to select hybrids with strong stalks, or to identify hybrids that have limited stalk strength.

BRIEF DESCRIPTION

FIG. 1 is a perspective view of a combine having the stalk testing device of the present invention attached thereto.

FIG. 2 is an enlarged perspective view of the stalk testing device.

FIG. 3 is a sectional view taken along lines 3—3 of FIG. 2.

FIG. 4 is a sectional view taken along lines 4—4 of FIG. 2.

FIG. 5 is a top plan view showing the testing device in an initial stalk engaging position.

FIG. 6 is a view similar to FIG. 5 showing the arm of the testing device pivoted rearwardly by a strong stalk, and showing in broken lines a weak stalk broken or pushed over by the arm of the device.

DETAILED DESCRIPTION OF THE DRAWINGS

The testing device of the present invention is generally designated in the drawings by the reference numeral 10. Device 10 can be mounted on any prime mover, such as a tractor or, as shown in the drawings, a combine 12 having a box beam frame 13.

Device 10 includes a frame 14, an upright member 16, and an extending arm 18. The end of arm 18 may be substantially horizontal or bent downwardly as shown in FIG. 4. Frame 14 has holes 15 drilled to match holes (not shown) in the prime mover frame 13. Device 10 is secured by dropping a pin 17 through one of the holes 15 in frame 14 and the aligned hole in the prime mover frame 13. Pin 17 is secured with a cotter pin 19 or the like. Frame 14 is thereby adjustably mounted upon combine 12 by sliding the frame in and out along the combine frame 13 and selecting the appropriate hole 13 in frame 14. Alternatively, a nut and bolt assembly can be used to mount device 10 on the prime mover.

Upright member 16 is pivotally connected to frame 14 by a bearing 26. The inner end of arm 18 has a collar 26 which is slidably received on upright 16. Collar 26 has a hole 28 extending therethrough which can be matingly aligned with one of a plurality of holes 30 extending through upright member 16. Thus, the height of arm 18 can be selectively adjusted, with the arm being locked in place by a pin 32 extending through holes 28, 30, and secured by a cotter pin 34.

A spring 36 is mounted on frame 14 so as to bias upright member 16 and attached arm 18 against pivotal movement. More particularly, spring 36 has a first end 38 which is attached to a flange 40, which is attached to upright member 16 through a lower arm assembly 42. The opposite end 44 of spring 36 is attached to a hollow collar 46 which is internally threaded or which has a threaded nut 48 welded thereto, as seen in FIGS. 3 and 4. A bolt 50 extends through a flange 52 extending from frame 14 and is threadably received within nut 48. The tension on spring 36 can be adjusted by turning bolt 50. The turning of bolt 50 in one direction pulls nut 48, and thus collar 46 and second end 44 of spring 36, towards flange 52 so as to increase the biasing tension of spring 36 against the pivotal movement of upright member 16 and arm 18. The turning of bolt 50 in the opposite direction decreases the tension of spring 36.

The angle of arm 18 with respect to frame 14 is also adjustable. More particularly, a flange 54 is attached to upright member 16 by welding or the like. A second flange 56 extends upwardly from frame 14 as spaced apart from flange 54. A nut and bolt assembly 58, 60 extends between flanges 54 and 56. The end of bolt 60 extends through a hole in flange 54. Bolt 60 is used to adjust the initial rest or at normal position of arm 18. Nut 58 is on the back side of flange 54 and locks the position of bolt 60. More particularly, the head of bolt 60 engages flange 56 while nut 58 is free to turn on bolt 60. As nut 58 is threaded down bolt 60, thereby increasing the spacing between flange 54 and flange 56, upright member 16 is pivoted in a counterclockwise direction, as seen in FIG. 3. When nut 58 is threaded up bolt 60, the space between flanges 54 and 56 is decreased, thereby allowing member 16 to pivot in a clockwise direction.

In operation, device 10 is mounted to combine 12, or to a tractor or other prime mover, and the height of arm 18 is selectively adjusted. The angle of arm 18 with respect to frame 14 is adjusted via nut and bolt assembly 58, 60. The biasing force of spring 36 is also adjusted via nut and bolt assembly 48, 50.

As the prime mover or combine 12 moves along a row of plants, such as corn, arm 18 engages the stalk of the plant. As the combine 12, and thus arm 18 continue to move forwardly with respect to the plant, a plant having a sufficiently strong stalk will pivot arm 18 rearwardly away from its at rest position, as seen in solid lines in FIG. 6. The strong stalk may also be pushed over without breaking. After the first end 38 of arm 18 moves past the stalk, the arm will be automatically returned to its initial position by the tension of spring 36. If a stalk is not sufficiently strong to resist the force of the forwardly moving arm, the stalk will be pushed over and broken by arm 18, as shown in broken lines in FIG. 6.

The percentage of stalks which are broken can be used to judge stalk strength of hybrids being developed. Thus, stalks having strong or weak limitations can be identified.

It is understood that the embodiment of device shown in the drawings and described above can be varied without departing from the scope of the present invention. For example, spring 36 could be replaced by a pneumatic or hydraulic cylinder. Also, holes 28 and 30, and pin 32 can be replaced by a set screw or other fastening means for adjustably connecting arm 18 to upright member 16. The structural design of the frame also can be modified in manners which accomplish the same results.

From the foregoing, it can be seen that the present invention accomplishes at least all of the stated objectives.

What is claimed is:

1. A method of testing the relative strength of a plant stalk, comprising:

engaging the stalk with an arm extending horizontally in a first position and having opposite first and second ends, the first end being operatively connected to a prime mover so as to be pivotal about a vertical axis;

moving the prime mover and arm forwardly whereby the arm pivots rearwardly to a second position when the stalk is sufficiently strong to resist the force of the forwardly moving arm, and whereby the arm pushes the stalk over when the stalk is not sufficiently strong to resist the force of the forwardly moving arm.

2. The method of claim 1 further comprising automatically returning the arm from the second position to the first position after the second end of the arm has moved out of engagement with the stalk.

3. The method of claim 18 further comprising normally urging the arm toward the first position.

* * * * *